(12) United States Patent
Kapre

(10) Patent No.: US 11,878,054 B2
(45) Date of Patent: Jan. 23, 2024

(54) VLP STABILIZED VACCINE COMPOSITIONS

(71) Applicant: Inventprise, LLC, Redmond, WA (US)

(72) Inventor: Subhash V. Kapre, Redmond, WA (US)

(73) Assignee: Inventprise, Inc., Redmond, WA (US)

( * ) Notice: Subject to any disclaimer, the term of this patent is extended or adjusted under 35 U.S.C. 154(b) by 0 days.

(21) Appl. No.: 16/988,659

(22) Filed: Aug. 9, 2020

(65) Prior Publication Data

US 2021/0069318 A1 Mar. 11, 2021

Related U.S. Application Data

(63) Continuation of application No. 15/257,143, filed on Sep. 6, 2016, now Pat. No. 10,758,606.

(60) Provisional application No. 62/214,526, filed on Sep. 4, 2015.

(51) Int. Cl.

| | |
|---|---|
| *A61K 39/29* | (2006.01) |
| *A61K 39/295* | (2006.01) |
| *A61K 47/42* | (2017.01) |
| *C07K 14/025* | (2006.01) |
| *A61K 39/12* | (2006.01) |
| *A61K 9/00* | (2006.01) |
| *A61K 9/19* | (2006.01) |
| *A61K 47/10* | (2017.01) |
| *C07K 14/005* | (2006.01) |
| *C12N 7/00* | (2006.01) |
| *A61K 39/00* | (2006.01) |

(52) U.S. Cl.
CPC ............ *A61K 39/12* (2013.01); *A61K 9/0019* (2013.01); *A61K 9/19* (2013.01); *A61K 47/10* (2013.01); *A61K 47/42* (2013.01); *C07K 14/005* (2013.01); *C12N 7/00* (2013.01); *A61K 2039/5258* (2013.01); *C12N 2710/20034* (2013.01); *C12N 2730/10123* (2013.01); *C12N 2730/10142* (2013.01)

(58) Field of Classification Search
None
See application file for complete search history.

(56) References Cited

U.S. PATENT DOCUMENTS

| | | | |
|---|---|---|---|
| 6,290,967 B1 | 9/2001 | Volkin et al. | |
| 6,922,172 B2 | 7/2005 | Oshiyama et al. | |
| 8,784,826 B2 | 7/2014 | Borkowski et al. | |
| 9,109,007 B2 | 8/2015 | Kyle et al. | |
| 9,439,958 B2 | 9/2016 | Arntzen et al. | |
| 2006/0127415 A1* | 6/2006 | Mayeresse | A61P 31/04 424/234.1 |
| 2011/0243988 A1* | 10/2011 | Ohtake | A61P 37/02 424/234.1 |
| 2013/0095134 A1 | 4/2013 | Arntzen et al. | |
| 2014/0056933 A1 | 2/2014 | Renner et al. | |
| 2016/0228532 A1 | 8/2016 | Bhambhani | |

FOREIGN PATENT DOCUMENTS

| | | |
|---|---|---|
| CA | 2352777 | 9/2009 |
| CN | 1332749 | 1/2002 |
| WO | WO2010001409 | 1/2010 |
| WO | WO2016/022916 | 2/2016 |

OTHER PUBLICATIONS

Beterams et al. (FEBS Letters 481 (2000) 169-176).*
Mcbride, A.A. Mechanisms and strategies of papillomavirus replication. Biol. Chem. 2017; 398(8): 919-927.*
Zhu et al. Hepatitis B virus surface antigen as delivery vector can enhance Chlamydia trachomatis MOMP multi-epitope immune response in mice. Appl Microbiol Biotechnol (2014) 98:4107-4117.*
Halperin et al. Safety and immunogenicity of a hexavalent diphtheria-tetanus-acellular pertussis-inactivated poliovirus-aemophilus influenzae b conjugate-hepatitis B vaccine at 2, 3, 4, and 12-14 months of age. Vaccine 27 (2009) 2540-2547.*
Search and Examination Reports of CN Application No. 201680062799.1 dated Sep. 30, 2021.
Search Report of CN Application No. 201680062799.1 dated Sep. 30, 2021. (translated).
Examination Report of CN Application No. 201680062799.1 dated Sep. 30, 2021. (translated).
Examination Report of ID Application No. PID201802200 dated Nov. 25, 2020.
Examination Report of ID Application No. PID201802200 dated Nov. 25, 2020 = translation.
Examination Report of ID Application No. PID201802200 dated Aug. 18, 2020.
Examination Report of ID Application No. PID201802200 dated Aug. 18, 2020 = translation.
Examination Report of MY Application No. PI2018700804 dated Mar. 29, 2021.
Examination Report of CN Application No. 201680062799.4 dated Apr. 6, 2021—translation.
Examination Report of CN Application No. 201680062799.4 dated Apr. 6, 2021.
Search Report of CN Application No. 201680062799.4 dated Apr. 6, 2021.

(Continued)

*Primary Examiner* — Nianxiang Zou
(74) *Attorney, Agent, or Firm* — Remenick PLLC

(57) ABSTRACT

The invention is directed to compositions and methods for the stabilization of viral and bacterial vaccines. Vaccines of the invention are contained in VLPs with stabilizing agents such as, for example, sugar alcohols (e.g., sorbitol) and degraded gelatins. Preferably the gelatin has an average molecular weight of 10,000 kilodaltons or less. These vaccines have a substantially improved thermostability as well as long term stability. The invention is also directed to the manufacture of a vaccine or the invention and methods for the administration of a vaccine of the invention to patients.

32 Claims, No Drawings

(56) References Cited

OTHER PUBLICATIONS

Search Report of CN Application No. 201680062799.4 dated Apr. 6, 2021—translation.
Cover sheets of Examination Report of CN Application No. 201680062799.4 dated Apr. 6, 2021—translation.
R.W. Tindle, Virology No. 2, pp. 47-557, 1994.
Examination Report of ID Application No. PID201802200 dated Mar. 11, 2020.
Examination Report of ID Application No. PID201802200 dated Mar. 11, 2020 -translation.
Examination Report of KR Application No. 10-2018-7008780 dated Nov. 25, 2019.
Examination Report of KR Application No. 10-2018-7008780 dated Nov. 25, 2019—machine translation.
Supplemental Search Report for EPO Application No. 16843179.9 dated Dec. 14, 2018.
Garry L. Morefield, A Rational Systemic Approach for the Development of Vaccine Formulations, The AAPS Journal, 13(2):191-200, Feb. 23, 2011.
Lihua Shen, Efficient Encapsulation of Fe3O4 Nanoparticles into Genetically Engineered Hepatitis B Core Virus-Like Particles through a Specific Interaction for Potential Bioamplifications, Small vol. 11(9-10):1190-1196, Mar. 1, 2015.
Subrat Kumar Panda, Recombinant Hepatitis E Virus Like Particles can Function as RNA Nanocarriers, Journal of Nanobiotechnology 13(1):44, Jun. 24, 2015.
Search Report and Written Opinion for PCT App. No. PCT/US16/50375 dated Dec. 1, 2016.
Schwardiz et al. Development of virus-like particles for diagnostic and prophylactic biomedical applicationsWiley Interdiscip Ren Nanomed Nanobiotechnol. Sep. 2015 ; 7(5): 722-735.
Beterams et al. Packaging of up to 240 subunits of a 17 kDa nuclease into the interior of recombinant hepatitis B virus capsids FEBS Letters 481 (2000) 169-176.
Tumban et al. A Pan-HPV Vaccine Based on Bacteriophage PP7 VLPs Displaying Broadly Cross-Neutralizing Epitopes from the HPV Minor Capsid Protein, L2. PloS One. 2011, 6(8): e23310.
Tindle et al. Chimeric hepatitis B core antigen particles containing B- and Th-epitopes of human papillomavirus type 16 57 protein induce specific antibody and T-helper responses in Immunized mice Virology 1994;200.647-667.
Office action for KR Application No. 10-2018-7008780 dated May 2, 2019.
Office action for KR Application No. 10-2018-7008780 dated May 2, 2019 (machine translation).
Examination Report for IN Application No. 201817007689 dated Nov. 11, 2020.
Examination Report of PH Application No. 1-2018-500458 dated Sep. 7, 2021.
Examination Report of BR Application No. BR 11 2018 004400 8 dated Dec. 23, 2020.
Examination Report of BR Application No. BR 11 2018 004400 8 dated Dec. 23, 2020—translation.
Examination Report of ID Application No. PID201802200 dated Jan. 4, 2022 = translation.
Examination Reports of CN Application No. 201680062799.1 dated Apr. 27, 2022.
Examination Report of CN Application No. 201680062799.1 dated Apr. 27, 2022. (translated).
Examination Report of MY Application No. PI2018700804 dated Oct. 31, 2022.
Search Report of MY Application No. PI2018700804 dated Oct. 31, 2022.

\* cited by examiner

VLP STABILIZED VACCINE COMPOSITIONS

REFERENCE TO RELATED APPLICATIONS

This application is a continuation of U.S. application Ser. No. 15/257,143 filed Sep. 6, 2016, which issued as U.S. Pat. No. 10,758,606 on Sep. 1, 2020, and claims priority to U.S. Provisional Application No. 62/214,526 entitled "VLP Stabilized Vaccine Compositions" filed Sep. 4, 2015, the entirety of which is specifically incorporated by reference.

BACKGROUND

1. Field of the Invention

The invention is directed to compositions and methods for stabilizing biological materials and, in particular, vaccines. In particular, the invention is directed to vaccines that are encapsulated within VLPs that contain an immunogenic or active component and a stabilizer. Preferred stabilizers include sugar alcohols sorbitol and degraded gelatins. The invention further relates to stabilized vaccines for the treatment or prevention of infections cause by bacterial, viral, parasitic or other infections and the manufacture of such vaccines.

2. Description of the Background

HPV, or human papillomavirus, is a human DNA virus of the papillomavirus family of viruses. Similar to other papillomaviruses, HPVs infects keratinocytes of the skin and mucous membranes. Typically, HPV infections are subclinical and cause little to no physical symptoms. Infections can become clinical and lead to the development of benign papilloma, also called warts or squamous cell papilloma. Clinical infections can also become cancerous developing into cancer of, for example, the throat and reproductive tissues such as the cervix.

A large majority of clinical HPV infections regress to subclinical in one to two years. In patients where the subclinical infection persists, which occurs in five to ten percent of infected women, there is high risk of developing precancerous lesions of the vulva and cervix that progress to invasive cancer. As progression from subclinical to clinical infection takes years, there are many opportunities for detection and treatment of pre-cancerous lesions.

In developed countries, cervical screening using a Papanicolaou (Pap) test or liquid-based cytology is used to detect abnormal cells that may develop into cancer. If abnormal cells are found, women are invited to have a colposcopy during which biopsies can be taken and abnormal areas removed. The removal of abnormal cells is highly effective in preventing the development of cervical cancer.

Two HPV vaccines are available, CERVARIX™ and GARDASIL™. Each prevents infection caused by HPV types 16 or 18. These two strains are believed to be responsible for over seventy percent of cervical cancers. As with all vaccines, HPV vaccines need to be stabilized during transportation and storage and therefore contain stabilizers. Stabilizers are chemical compounds added to a vaccine formulation to enhance vaccine stability during low temperature storage or storage post-lyophilization.

One such chemical stabilizer is referred to as SPGA and contains 218 mM sucrose, 3.76 mM $KH_2PO_4$, 7.1 mM $K_2HPO_4$, 4.9 mM potassium glutamate, and 1% serum albumin. Modifications of SPGA include monosodium glutamate as a substitute for monopotassium glutamate, starch hydrosylate such as glucose or dextran as a substitute wholly or partly for sucrose, and casein or PVP substituted wholly or partly for albumin. Another well-known chemical stabilizer comprises approximately 3.5% hydrolyzed gelatin, 3.5% sorbitol, 1.0% Medium 199, along with minimal amounts of sodium bicarbonate and phenol red. Other stabilizers comprise minute amounts of DPG solution, which contains, among other compounds, cysteine, glutathionine, ascorbic acid, vitamin A and USP. Additional processes and stabilizing agents are disclosed in U.S. Pat. Nos. 3,985,615; 3,915,794; 4,000,256; 4,147,772; 4,537,769; 4,555,401; 4,849,358; 4,985,244; 5,139,776; 7,998,488; 8,142,795; 8,551,523; 8,557,253; 8,795,683 and International Application Publication No. WO1998028000, each of which is incorporated herein by reference.

Nevertheless, all of these stabilizers have shortcomings, either an inability to maintain stability in higher temperatures or fail after a period of time less than optimal. Thus, a need currently exists for an effective stabilization chemical formulation and/or process that maintains immunogenicity of the vaccine and imparts no side effects.

SUMMARY OF THE INVENTION

In general, the invention is directed to compositions and methods for stabilizing vaccine formulation and especially human papilloma virus (HPV) vaccines.

One embodiment of the invention is directed to vaccines comprising VLPs (virus like particles) that encapsulate an immunogenic component and a stabilizing agent. The immunogenic component comprises the immune-stimulating portion or active portion of the vaccine that generates an immune response. Preferred immune stimulating portions include immunogenic portions of an infectious virus, bacterium or parasite. Preferred VLPs comprise structural components of a virus such as, for example, the structural components of hepatitis virus or human papilloma virus (HPV), and VLP do not contain genetic material that permits replication of particles. Preferably the stabilizing agent comprises one or more gelatins, one or more amino acids, or one or more sugar alcohols, or any combination thereof. Preferred gelatins are degraded chemically or mechanically to fragments with an average molecular weight of ten kilodaltons or less, or eight kilodaltons or less. Also preferably, vaccines of the invention do not require the addition of aluminum compounds such as aluminum phosphate. Vaccines of the invention may be maintained for long periods of time as a liquid, or even longer periods of time as a lyophilized powder. Preferred vaccines further contain pharmaceutically acceptable carriers such as, for example, an alcohol, propylene glycol, fatty alcohols, triglycerides, fatty acid esters, mineral oils, liquid petrolatum, isopropylpalmitate, polyethylene ethanol, polyoxyethylene monolauriater, sodium lauryl sulfate, an anti-oxidant, a humectant, a viscosity stabilizer or modifier, a colorant or a flavoring agent.

Another embodiment of the invention is directed to methods for the administration of stabilized vaccines of the invention to a patient. Preferred patients are mammals that have a functioning immune system. Methods comprise determining the therapeutically effective amount of the vaccine to be administered, and administering that amount of the vaccine to a patient in need thereof. Preferably the vaccine is a lyophilized powder and reconstituted to an aqueous or non-aqueous liquid prior to administration to the patient. Also preferably the vaccine is administered as a liquid and administering is intra-muscular, intra-peritoneal, or intra-venous. Preferred patients include, but are not limited to an infant, a toddler, an adolescent, an adult or a senior. Preferably administration of a vaccine of the invention does not generate a general inflammation response in the patient or local inflammation at the site of administration.

Another embodiment of the invention is directed to methods for the manufacture of stabilized vaccines of the invention comprised of VLPs, an immunogenic agent, and a stabilizing agent, comprising: generating VLP comprising structural components of human hepatitis virus; mixing the components with an immunogenic agent and a stabilizing agent; and forming VLPs that encapsulate the immunogenic agent and the stabilizing agent. Preferably the structural components, the immunogenic agent and the stabilizing agent are mixed at approximately equimolar amounts. Also preferably the VLPs that encapsulate the immunogenic agent and the stabilizing agent are in an aqueous mixture. Preferably manufacturing comprising lyophilizing the aqueous mixture. Also preferably, no aluminum-containing compounds are added to the vaccine composition.

Other embodiments and advantages of the invention are set forth in part in the description, which follows, and in part, may be obvious from this description, or may be learned from the practice of the invention.

DESCRIPTION OF THE INVENTION

There are many vaccines that are currently available that provide protection against viral and bacterial infections. Each of these vaccines contains various non-active components that increase stability and maintain the effectiveness of the vaccine over periods of time.

It has been surprisingly discovered that vaccine stability can be increased by containing the vaccine in a virus-like particle (VLP). Preferably VLPs contain the immunogenic component of the vaccine plus one or more stabilizers and one or more pharmaceutically acceptable carriers. Preferred stabilizers include sorbitol, amino acids, gelatin degraded to an average molecular weight of 10,000 MW or less, or combinations thereof. Increased stability includes an increased thermostability and an increased stability over time. Although the increased stability herein is stated in reference to HPV vaccines, as is believed to be clear to those skilled in the art, the increased stability is equally applicable to most any vaccine composition including vaccines to prevent or treat viral, bacterial, parasitic and/or other infections.

Virus-like particles are comprised of viral structural proteins and resemble viruses, but are non-infectious and unable to replicate as they contain no viral genetic material. The VLPs self-assemble from expression of the viral structural proteins, such as, for example, envelope or capsid proteins in vitro such as for example in a test tube, and/or in vivo such as for example in cell culture. VLPs of the invention are preferably derived from hepatitis virus (e.g., Hepatitis B virus) and composed of the small HBV derived surface antigen (HBsAg), but may also be derived from the structural components of parvoviruses (e.g. adeno-associated virus), retroviruses (e.g. HIV), vesicular stomatitis virus (e.g., VSV), hepatitis virus (e.g. hepatitis A, B, C, D or E virus), flaviviruses (e.g., West Nile virus, dengue virus, tick-borne encephalitis virus, yellow fever virus, Zika virus and several other viruses that cause encephalitis), and combinations thereof. VLPs can be produced in a variety of cell culture systems including mammalian cell lines, insect cell lines, yeast cell lines, and plant cell lines. VLPs may be formed in a buffered solution containing one or more of chelating and/or reducing agents.

Accordingly, one embodiment of the invention is directed to a vaccine containing an immunogenic agent and a stabilizing agent encapsulated into a VLP. The immunogenic agent of the VLP comprises an antigen or other structure that stimulates an immune response in an individual. Immunogenic agents include, but are not limited to peptides, proteins, lipids, fatty acids, polysaccharides, lipopolysaccharides. Typically, immunogenic agents are surface antigens of an infectious particle. Antigens may be specific for a particular infectious agent or combination of agents such as, for example, viral infectious agents (e.g., enterovirus, hepatitis virus, human immunodeficiency virus {HIV}, human papilloma virus {HPV}, influenza virus, pertussis virus, rubella virus, tetanus, varicella virus {VZV}, flavivirus, West Nile virus, dengue virus, tick-borne encephalitis virus, yellow fever virus, Zika virus), bacterial infectious agents (e.g., chlamydia, clostridium, diphtheria, meningococcal, streptococcal, staphylococcal, pneumococcal), parasitic infectious agents (e.g., giardia, malaria {plasmodium}), and/or an agent that causes sepsis or septicaemia. Preferably the immune response is sufficient to protect the individual from subsequent infections for a period of time. Preferably the vaccine is effective and protects a patient from infection for six months or greater, one year or greater, two years or greater, five years of greater, or ten years or greater The immune response generated in response to the immunogenic agent of the invention generates a humoral immune response, a cellular immune response, or preferably both in the individual. Preferred cellular response include a T cell response, and/or a phagocytic response, and also preferably a memory cell response.

Preferred stabilizing agents to include in VLPs of the invention include, but are not limited to one or more of carbohydrates such as glucose and/or fructose, sugar alcohols such as glycerol, erythritol, threitol, avabitol, xylitol, ribitol, mannitol, galactitol, fucitol, iditol, inositol, volemitol, isomalt, lacitol, sorbitol, maltotriitol, maltotetraitol, polyglyitol or dextrin, dehydrated sugar alcohols such as isosorbide, amino acids such as arginine, proline, and/or lysine, substituted amino acids such as hydroxyl-alanine, animal-derived gelatins such as human collagen, BSA, and/or fish gelatin, and/or plant-derived carbohydrates such as pectin and cellulose. Preferably gelatins of the invention are degraded to an average molecular weight of 100 kilodaltons (kD) or less, 50 kD or less, 20 kD or less, 10 kD or less, 8 kD or less, or 5 kD or less. Also preferably, vaccines of the invention do not require the addition of aluminum, magnesium or manganese compounds such as aluminum phosphate or other forms of aluminum, magnesium or manganese, or preferably any metal compound. Stabilizing agents may be added at from 1-10% of the dry weight of the VLP components, or from 1-10% of the dry weight of the VLP components plus the immunogenic agent, or preferably from 2-4% of the dry weight of either composition. Also preferably, the stabilizing agent is at a concentration of from 1 mM to 50 mM of the aqueous mixture, preferably at a concentration of from 10-20 mM.

Preferably the vaccine is maintained as a liquid, but the liquid may be lyophilized and stored as a dry powder until use wherein the powder is rehydrated in an appropriate carrying agent (aqueous or non-aqueous) for administration to the individual. Administration is preferable by injection which may be intra peritoneal (i.p.), intra muscular (i.m.), and/or intra venous (i.v.), or localized to the site of an infection.

Preferably the vaccines of the invention as liquids or powders are stable at 4° C. or greater, 15° C. or greater, 25° C. or greater, 37° C. or greater, 40° C. or greater, 50° C. or greater, or 100° C. or greater. Also preferably, the vaccines of the invention as liquids or powers are stable at 15° C. or less, more preferably to 0° C. or less, more preferably to minus 20° C. or less, and more preferably to minus 50° C. or less. Also preferably, stability of the vaccines is maintained for six month or greater, for eight months or greater or for twelve months or greater. Preferably the vaccines of the invention are stable through varying temperatures over time which may include multiple freezing and thawing.

Another embodiment of the invention is directed to methods for the administration of vaccines of the invention to patients in need thereof for treating or preventing an infection. The method comprises administering a therapeutically effective amount of the vaccine of the invention to a mammal, comprising determining the therapeutically effective amount of the vaccine to be administered. The therapeutically effective amount is typically determined by based on the weight of the mammal and the strength and responsiveness of the patient's immune system and can be determined by those skilled in the art. The therapeutically effective amount is administered to a patient in need thereof, which may be to treat an active or suspected infection or prevent an infection. The vaccine may have been obtained from a lyophilized powder and reconstituted to an aqueous or non-aqueous liquid prior to administration to the patient. Preferably the vaccine is administered as a liquid, which may be intra-muscular, intra-peritoneal, or intra-venous, and the patient may be an infant, a toddler, an adolescent, an adult or a senior. Surprisingly, the vaccine of the invention does not generate side effects such as redness or inflammation at the injection site, and does not generate a generalized fever or inflammation, or other unwanted side effects for the patient. Preferably an immunologically effective vaccine contains only the fully formed VLPs containing immunogenic and stabilizing agents, and nothing further such as, for example, no added ionic or non-ionic surfactants.

Another embodiment of the invention is directed to method for the manufacture of vaccines of the invention. Structural components of viruses are obtained by methods well known to those skilled in the art and exclusive of any nucleic acid material that would allow the components and resulting particles to replicate. Predetermined molar amounts of the structural components are mixed, preferably at room temperature or below, with approximately equivalent molar amounts of one or more immunogenic agents and one or more stabilizing agents of the invention, such that the VLPs encapsulate the one or more immunogenic agents and the one or more stabilizing agents in roughly equivalent amounts. The fully formed VLPs are separated from unformed VLPs and free structural and other materials preferably by filtration, centrifugation or another method known to those skilled in the art, thereby creating fully formed VLPs containing one more immunogens and one or more stabilizing agents. The fully formed VLPs may be stored as an aqueous (e.g., water or saline) or non-aqueous (e.g., oils, fatty acids) mixture, or lyophilized and stored as a powder. Preferably storage until use is without significant loss of immunogenic activity and, for example, may be for one month or longer, four months or longer, six months or longer, or more preferably one year or longer and at ambient temperatures, whether as a liquid or a powder. Storage of vaccine without loss of immunogenic activity may also be at less than ambient temperature such as, for example, at 20° C. or less, at 10° C. or less, at 4° C. or less, or at 0° C. or less.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. A liquid composition comprising virus-like particles (VLPs), an immunogenic component and a stabilizing agent comprised of one or more gelatins degraded to an average molecular weight of about twenty kilodaltons or less, wherein the immunogenic component is a Staphylococcal polysaccharide antigen, wherein the composition is maintained as a liquid and as a liquid stored at ambient temperatures without significant loss of immunogenic activity, and wherein the composition has not been maintained in a non-liquid state.

2. The composition of claim 1, wherein the VLPs are obtained from the structural components of a virus.

3. The composition of claim 2, wherein the virus is hepatitis virus or human papilloma virus.

4. The composition of claim 1, further comprising one or more amino acids, or one or more sugar alcohols, or any combination thereof.

5. The composition of claim 1, wherein the one or more gelatins are degraded chemically or mechanically.

6. The composition of claim 5, wherein the one or more degraded gelatins are degraded to an average molecular weight of ten kilodaltons or less.

7. The composition of claim 5, wherein the one or more degraded gelatins are degraded to an average molecular weight of eight kilodaltons or less.

8. The composition of claim 4, wherein the one or more sugar alcohols comprises sorbitol.

9. The composition of claim 1, which does not contain an aluminum compound.

10. The composition of claim 1, wherein the VLP comprises the structural components of hepatitis virus and the composition does not contain an aluminum compound.

11. The composition of claim 1, which further contains a pharmaceutically acceptable carrier selected from the group consisting of alcohol, propylene glycol, fatty alcohols, triglycerides, fatty acid esters, mineral oils, liquid petrolatum, isopropylpalmitate, polyethylene ethanol, polyoxyethylene monolauriater, sodium lauryl sulfate, an anti-oxidant, a humectant, a viscosity stabilizer or modifier, a colorant or a flavoring agent.

12. The composition of claim 1, which remains immunogenic at temperatures from 4° C. to 50° C.

13. The composition of claim 1, which remains immunogenic through freezing and thawing.

14. The composition of claim 1, which is a vaccine.

15. A liquid composition comprising one or more structural components that form virus-like particles (VLPs) and an immunogenic component, wherein the composition comprises a degraded gelatin with an average molecular weight of from about twenty kilodaltons to about 5 kilodaltons, the one or more structural components are obtained from a virus, and the immunogenic component is a viral antigen selected from the group of viruses consisting of enterovirus, hepatitis virus, human immunodeficiency virus (HIV), human papilloma virus (HPV), influenza virus, pertussis virus, rubella virus, tetanus, varicella virus (VZV), flavivirus, West Nile virus, dengue virus, tick-borne encephalitis virus, yellow fever virus, and Zika virus, wherein the composition is maintained as a liquid and as a liquid stored at ambient temperatures without significant loss of immunogenic activity, and wherein the composition has not been maintained in a non-liquid state.

16. The composition of claim 15, wherein the VLPs are obtained from hepatitis virus or human papilloma virus.

17. The composition of claim 15, wherein the immunogenic agent comprises a peptide, a protein, a lipid, a fatty acid, a polysaccharide, or a lipopolysaccharide.

18. The composition of claim 15, which does not contain an aluminum compound.

19. The composition of claim 15, wherein the degraded gelatin has an average molecular weight of ten kilodaltons or less.

20. The composition of claim 15, wherein the degraded gelatin has an average molecular weight of eight kilodaltons or less.

21. The composition of claim 15, which is a vaccine.

22. A liquid composition comprising one or more structural components obtained or derived from hepatitis virus or human papilloma virus that form virus-like particles (VLPs) and an immunogenic component and a stabilizing agent, wherein the stabilizing agent is a degraded gelatin with an average molecular weight of twenty kilodaltons or less, and does not contain an aluminum compound, wherein the immunogenic component is a Streptococcal polysaccharide antigen and the composition is stored at ambient temperatures as a liquid without significant loss of immunogenic activity, and wherein the composition has not been maintained in a non-liquid state.

23. The composition of claim 22, which is a vaccine.

24. The composition of claim 1, wherein storage is for at least 6 months.

25. The composition of claim 15, wherein storage is for at least 6 months.

26. The composition of claim 22, wherein storage is for at least 6 months.

27. The composition of claim 1, wherein there is no loss of immunogenic activity after storage for four months.

28. The composition of claim 15, wherein there is no loss of immunogenic activity after storage for four months.

29. The composition of claim 22, wherein there is no loss of immunogenic activity after storage for four months.

30. The composition of claim 1, which, upon administration to a patient, does not generate a general inflammation response or local inflammation at the site of administration.

31. The composition of claim 15, which, upon administration to a patient, does not generate a general inflammation response or local inflammation at the site of administration.

32. The composition of claim 22, which, upon administration to a patient, does not generate a general inflammation response or local inflammation at the site of administration.

\* \* \* \* \*